United States Patent
Bruchmann et al.

(10) Patent No.: US 6,617,413 B1
(45) Date of Patent: Sep. 9, 2003

(54) COATING AGENTS WHICH CAN BE HARDENED BY THE ADDITION OF ISOCYANATE GROUPS AS WELL AS BY THE RADIATION-INDUCED ADDITION OF ACTIVATED C-C DOUBLE COVALENT BONDS

(75) Inventors: Bernd Bruchmann, Freinsheim (DE); Erich Beck, Ladenburg (DE); Hans Renz, Meckenheim (DE); Rainer Königer, Ludwigshafen (DE); Reinhold Schwalm, Wachenheim (DE); Matthias Lokai, Enkenbach-Alsenborn (DE); Wolfgang Reich, Maxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/868,712
(22) PCT Filed: Dec. 14, 1999
(86) PCT No.: PCT/EP99/09905
§ 371 (c)(1), (2), (4) Date: Aug. 29, 2001
(87) PCT Pub. No.: WO00/39183
PCT Pub. Date: Jul. 6, 2000

(30) Foreign Application Priority Data
Dec. 23, 1998 (DE) .......................... 198 60 041

(51) Int. Cl.$^7$ ............................... C08G 83/00
(52) U.S. Cl. ............ 528/75; 252/182.2; 560/25; 156/275.5; 427/508; 522/90; 522/96; 428/423.1
(58) Field of Search ................. 252/182.2; 560/25; 156/275.5; 528/75; 427/508; 522/90, 96; 428/423.1

(56) References Cited

U.S. PATENT DOCUMENTS

| | | | | |
|---|---|---|---|---|
| 4,751,145 A | * | 6/1988 | Sebastiano et al. |
| 5,011,560 A | * | 4/1991 | Nakai et al. |
| 5,739,251 A | * | 4/1998 | Venham et al. |
| 5,767,220 A | * | 6/1998 | Venham et al. |

FOREIGN PATENT DOCUMENTS

| | | | |
|---|---|---|---|
| EP | 549116 | * | 6/1993 |
| EP | 683189 | * | 11/1995 |
| JP | 61243815 | * | 10/1986 |

* cited by examiner

Primary Examiner—Rachel Gorr
(74) Attorney, Agent, or Firm—Oblon, Spivak, McClelland, Maier & Neustadt, P.C.

(57) ABSTRACT

Compounds having isocyanate groups with or without blocking, allophanate groups and free-radically polymerizable C—C double bonds, the C—C double bonds being in activated form by virtue of a carbonyl group attached directly to them or by virtue of an oxygen atom in ether function (activated double bonds), derived from polyisocyanates and alcohols A which in addition to the alcohol group also carry an activated double bond (compounds I). The invention additionally relates to radiation-curable formulations and coating compositions comprising the compounds I, to methods for coating using these substances, and to coated articles produced using these methods. Furthermore, the invention relates to the use of the compounds I in radiation-curable compositions such as in casting compositions, dental compounds, composite materials, sealing compounds, adhesives, troweling compounds, printing inks, in photo-structurable compositions such as solder resists, photoresists, photopolymeric printing plates, and stereolithography resins.

34 Claims, No Drawings

COATING AGENTS WHICH CAN BE HARDENED BY THE ADDITION OF ISOCYANATE GROUPS AS WELL AS BY THE RADIATION-INDUCED ADDITION OF ACTIVATED C-C DOUBLE COVALENT BONDS

The invention relates to compounds having isocyanate groups with or without blocking, allophanate groups and free-radically polymerizable C—C double bonds, the C—C double bonds being in activated form by virtue of a carbonyl group attached directly to them or by virtue of an oxygen atom in ether function (referred to for short below as activated double bonds), derived from polyisocyanates and alcohols A which, in addition to the alcohol group, also carry an activated double bond (compounds I).

The invention additionally relates to radiation-curable formulations and coating compositions which comprise the compounds I, to methods of coating with these substances, and to coated articles produced by these methods.

Coating compositions based on compounds containing isocyanate groups are common knowledge, for example, in the form of two-component coating materials (cf. Kunststoff Handbuch, Volume 7, Polyurethane, $2^{nd}$ edition, 1983, Carl-Hanser-Verlag München Vienna, pages 540–561). Industrial processors of coating systems, such as the coatings industry, expect said systems to meet a diverse profile of requirements. These requirements relate both to the processing properties and the service properties.

In terms of the processing properties it is very important that the coating systems combine a very low solvent content with a low viscosity. The low viscosity is required so that the coating materials can be applied without problems by customary techniques, such as by spraying, to the surface that is to be coated. The solvent content of these coating materials causes problems in that, when the coating materials are being processed, technically complex measures must be taken to ensure that the solvents released when the coating materials are applied and are drying are not emitted into the atmosphere.

Furthermore, it should be possible to cure the articles provided with the coating compositions by means of UV irradiation. In particular, following brief irradiation with relatively low radiation doses, the hardness should increase dramatically, but without longer irradiation leading to a further marked increase in hardness. With the prior art systems this hardening can be brought about only at very high radiation doses; in other words, the required dwell times in the existing irradiation units are still too long. There is therefore a need for systems having groups which on exposure to very low radiation doses, i.e. short exposure times, are consumed near-quantitatively in a polymerization reaction.

Furthermore, processors are increasingly calling for what are known as dual-cure systems. The feature of these systems is that they can be cured both by radiation and by means of a second, independent curing mechanism. There is a particular desire for systems which, following application of the coating composition, can be initially cured by very brief exposure to UV light to form a dust-dry film. Over the course of several days this film should then cure further, simply by storing it in air at room temperature or with heating, until a hard film is formed which has the ultimate desired service properties. This type of dual-stage curing is particularly important since it gives the processors of the coating systems the option to coat an article with a film in a first working step and then to process this film further in a second working step; in particular, to give the coated article following irradiation a defined profile using pressure. At the time of their deformation in the second working step, therefore, the films or foils must be already cured, so that they do not stick to the tools in the course of deformation; on the other hand, however, they must not be so hard as to crack when extended and deformed. The coated articles produced in this way must be stored for a while thereafter until the coating has attained its ultimate service properties.

As far as the service properties are concerned, particular requirements here are as follows.

- insensitivity to mechanical stress such as tension, extension, impact, scratching or abrasion;
- resistance to moisture (e.g., in the form of water vapor), solvents, petrol and dilute chemicals, as well as chemical environmental influences such as sulfuric acid rain, pancreatine, tree resin;
- resistance to environmental influences such as temperature fluctuations and UV radiation;
- high gloss of the coated surfaces;
- good adhesion to a variety of substrates such as
- good adhesion to a variety of substrates such as substrates coated beforehand with primers, fillers, color effect layers or other coatings, and also directly to plastics, wood, woodbase materials, paper, glass, ceramic, textiles, leather or metal.
- A further requirement is complete curability of unexposed or non-radiation-curable areas of the coating materials, for example in shaded regions of, for example, three-dimensional substrates such as vehicle bodies or pores in wood, paper, foams, ceramic materials, in coating materials containing radiation-absorbing ingredients such as pigments, UV absorbers, fillers, and of spray mist deposits. Curing is intended to take place in the course of storage in air or with additional heating or baking.

The applications DE-A-19741781 and DE-A-19814874, which were not published before the priority date of the present specification, relate to radiation-curable prepolymers which contain urethane groups and are used as coating compositions. However, they contain no free isocyanate groups.

U.S. Pat. No. 5,300,615 and U.S. Pat. No. 5,128,432 likewise disclose polyurethanes having free-radically polymerizable double bonds, but these likewise carry no free isocyanate groups.

EP-A-549116 and DE-A-3819627 relate to compounds which include both isocyanate groups and free-radically polymerizable C—C double bonds. These compounds are prepared by dimerizing or trimerizing commercially customary aliphatic isocyanates to give their counterparts having uretdione, isocyanurate or biuret groups, and then reacting these dimers and/or trimers with hydroxyalkyl acrylates. A disadvantage of these systems is that they have a very high viscosity and can be processed only with the addition of large amounts of solvent.

U.S. Pat. No. 5,739,251 likewise discloses urethanes formed from alcohols and comprising beta,gamma-ethylenically unsaturated ether groups, which are virtually free from isocyanate groups, and discloses allophanates derived from these urethanes.

These beta,gamma-unsaturated compounds, however, have the particular disadvantage of a high viscosity, and cannot per se be cured by means of UV radiation.

It is an object of the present invention to provide compounds which can be used to produce coating systems having the abovementioned profile in respect of the processing and service properties. In particular, the coating systems should possess a low viscosity at low solvent content and should be suitable for use as dual-cure systems whose radiation curing can be carried out completely (or until freedom from tackiness or scratch resistance of the films) with relatively low radiation doses.

We have found that this object is achieved using the compounds I of the invention which are in general essentially free from uretdione, biuret or isocyanurate groups.

Preferred compounds I are, therefore, those of the formula I

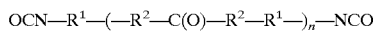

in which n is an integer from 1 to 10, preferably from 1 to 5

$R^1$ is a divalent aliphatic or alicyclic $C_2$–$C_{20}$ hydrocarbon unit or an aromatic $C_5$–$C_{20}$ hydrocarbon unit $R^2$ in each repeating unit is —NH— once and N—C(O)— $R^3$ once, $R^3$ being a radical derived from an alcohol by abstracting the hydrogen atom of the alcoholic hydroxyl group, and the alcohol carrying functional groups including, in addition to the alcohol group, an activated double bond.

The radicals $R^1$ are preferably those derived by extracting the isocyanate group from customary aliphatic or aromatic polyisocyanates. The diisocyanates are preferably aliphatic isocyanates of 4 to 20 carbon atoms. Examples of customary diisocyanates are aliphatic diisocyanates such as tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, tetramethylxylylene diisocyanate, trimethylhexane diisocyanate or tetramethylhexane diisocyanate, cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane or 2,4- or 2,6-diisocyanato-1-methylcyclohexane, and also aromatic diisocyanates such as 2,4- or 2,6-tolylene diisocyanate, m- or p-xylylene diisocyanate, 2,4'- or 4,4'-diisocyanatodiphenylmethane, 1,3- or 1,4-phenylene diisocyanate, 1 chloro-2,4-phenylene diisocyanate, 1,5-naphthylene diisocyanate, diphenylene 4,4'-diisocyanate, 4,4'-diisocyanato-3,3'-dimethylbiphenyl, 3-methyldiphenylmethane 4,4'-diisocyanate or diphenyl ether 4,4'-diisocyanate. Mixtures of said diisocyanates may also be present. Preference is given to hexamethylene diisocyanate, 1,3-bis(isocyanatomethyl)cyclohexane, isophorone diisocyanate, tetramethylxylylene diisocyanate, and di(isocyanatocyclohexyl)methane.

The alcohols A from which the radical $R^3$ is derived are, for example, esters of α,β-unsaturated carboxylic acids, such as acrylic acid, methacrylic acid (referred to below for short as (meth)acrylic acid), crotonic acid, acrylamidoglycolic acid, methacrylamidoglycolic acid or vinylacetic acid and polyols having preferably 2 to 20 carbon atoms and at least 2 hydroxyl groups, such as ethylene glycol, diethylene glycol, triethylene glycol, 1,2-propylene glycol, 1,3-propylene glycol, 1,3-propylene glycol, dipropylene glycol, tripropylene glycol, 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, glycerol, trimethylethane, trimethylolpropane, trimethylolbutane, pentaerythritol, ditrimethylolpropane, erythritol and sorbitol, provided the ester has at least one isocyanate-reactive OH group. The radicals $R^3$ may also be derived from the amides of (meth)acrylic acid with amino alcohols, examples being 2-aminoethanol, 3-amino-1-propanol, 1-amino-2-propanol and 2-(2-aminoethoxy)ethanol, and from the vinyl ethers of the above mentioned polyols, provided they still have one free OH group.

Further suitable reactive components are unsaturated polyetherols or polyesterols or polyacrylate polyols having an average OH functionality of from 2 to 10.

The radicals $R^3$ are preferably derived from alcohols such as 2-hydroxyethyl (meth)acrylate, hydroxypropyl (meth)acrylate, 1,4-butanediol mono(meth)acrylate, neopentyl glycol mono(meth)acrylate, glycerol mono- and di(meth)acrylate, trimethylolpropane mono- and di(meth)acrylate, and pentaerythritol di- and tri(meth)acrylate. With particular preference the alcohol A is selected from 2-hydroxyethyl acrylate, 2-hydroxyethyl methacrylate, hydroxypropyl acrylate, 1,4-butanediol monoacrylate and 3-(acryloyloxy)-2-hydroxypropyl methacrylate. Examples of amides of ethylenically unsaturated carboxylic acids with amino alcohols are hydroxyalkyl(meth)acrylamides such as N-hydroxymethylacrylamide, N-hydroxymethylmethacrylamide, N-hydroxyethylacrylamide, N-hydroxyethylmethacrylamide, 5-hydroxy-3-oxopentyl (meth)acrylamide, N-hydroxyalkylcrotonamides such as N-hydroxymethylcrotonamide, or N-hydroxyalkylmaleimides such as N-hydroxyethylmaleimide.

The isocyanate groups of the compounds I can also be present in blocked form. Examples of suitable blocking agents for NCO groups are oximes, phenols, imidazoles, pyrazoles, pyrazolinones, diketopiperazines, caprolactam, malonates or compounds as specified in the publications by Z. W. Wicks, Prog. Org. Coat. 3 (1975) 73–99 and Prog. Org. Coat. 9 (1981) 3–28 and also in Houben-Weyl, Methoden der Organischen Chemie, Vol. XIV/2, p. 61 ff., Georg Thieme Verlag, Stuttgart 1963.

The compounds I are employed preferably in the form of mixtures (mixtures I) comprising a1) from 1 to 100% by weight of compounds I a2) from 0 to 99% by weight of another compound which in addition to one or more isocyanate groups includes a group selected from the series consisting of urethane, urea, biuret, allophanate, carbodiimide, uretonimine, uretdione and isocyanurate groups.

Isocyanates which may be present in the mixtures I in addition to the compounds I are aliphatic and aromatic diisocyanates and, in particular, polyisocyanates of higher functionality (polyisocyanates a2) from the following groups:

a2.1) Polyisocyanates which contain isocyanurate groups and are derived from aliphatic, cycloaliphatic, aromatic and/or araliphatic diisocyanates, which may also be used to synthesize the compounds I. The isocyanatoisocyanurates generally have an NCO content of from 10 to 30% by weight, in particular from 15 to 25% by weight, and an average NCO functionality of from 2.6 to 4.5 (isocyanates a2.1). Particularly suitable are isocyanurates of the formula (II)

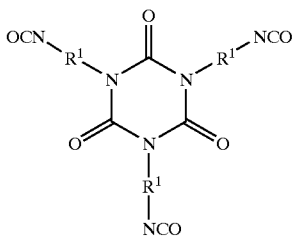

or the oligomeric forms deriving from them, where $R^1$ is as defined for compounds of the formula I.

a2.2) Diisocyanates which contain uretdione groups and have isocyanate groups attached to aromatic, aliphatic and/or cycloaliphatic structures, preferably derive from hexamethylene diisocyanate or isophorone diisocyanate. Polyuretdione diisocyanates are dimerization products of the diisocyanates (isocyanates a2.2).

a2.3) Polyisocyanates which contain biuret groups and have isocyanate groups attached to aliphatic structures, especially tris(6-isocyanatohexyl)biuret or its mixtures with its higher homologs. These biuret polyisocyanates generally have an NCO content of from 10 to 30% by weight, in particular from 18 to 25% by weight, and an average NCO functionality of from 2.8 to 4.5 (isocyanates a2.3)

a2.4) Polyisocyanates containing urethane and/or allophanate groups, and having isocyanate groups attached to aliphatic or cycloaliphatic structures, which are free from free-radically polymerizable C—C double bonds, where the C—C double bonds are in activated form by virtue of a carbonyl group attached directly to them or by virtue of an oxygen atom in ether function. Compounds of this kind are obtainable, for example, by reacting excess amounts of hexamethylene diisocyanate or isophorone diisocyanate with monohydric or polyhydric $C_1$–$C_{20}$ monoalcohols, polyhydric alcohols such as ethylene glycol, trimethylolpropane, glycerol or mixtures thereof. These polyisocyanates containing urethane and/or allophanate groups generally have an NCO content of from 12 to 25% by weight and an average NCO functionality of from 2.5 to 4.5 (isocyanates a2.4).

a2.5) Isocyanates derived from one molecule of an alcohol A and one molecule of a polyisocyanate as used to prepare the compounds I (isocyanates a2.5).

a2.6) Polyisocyanates which contain oxadiazinetrione groups, preferably derived from hexamethylene diisocyanate or isophorone diisocyanate. Polyisocyanates of this kind containing oxadiazinetrione groups can be prepared from diisocyanate and carbon dioxide (isocyanates a2.6).

a2.7) Carbodiimide- or uretonimine-modified polyisocyanates (isocyanates a2.7).

Some of the isocyanate groups of said polyisocyanates (a2.1) to (a2.7) can also have been reacted with monoalcohols.

The activated double bond content of the compounds I, based on the overall amount of the co-components a1 and a2, is generally from 0.002 to 20% by weight and, preferably, from 0.01 to 10% by weight.

The isocyanate group content of components a1 and a2, based on the overall amount of the co-components a1 and a2, is generally from 0.1 to 40, and, preferably, 1–30% by weight.

The molar masses assumed are 24 g/mol when stating the double bond content and 42 g/mol when stating the isocyanate content in % by weight.

The ratio of the activated double bonds of the compounds I to the isocyanate groups of the co-components a1 and a2 is generally from 50:1 to 0.02:1 and preferably from 10:1 to 0.1:1.

Particular preference is given to mixtures I comprising components a1 and a2.1 to a2.7 in the following composition:

Component a1: 5–95% by weight
Component a2.1: 5–60% by weight
Component a2.5: 0–60% by weight The mixtures I customarily have viscosities (measured at 23° C.) of less than 50,000 mPas, preferably 100–30,000 mPas.

The compounds I can be prepared by reacting the polyisocyanates and the alcohols A from which the compounds I are derived at reaction temperatures from 0 to 280° C., preferably from 20 to 250° C., in the presence of a catalyst which promotes the formation of allophanate, i.e., for example, an organozinc compound, such as zinc acetylacetonate or zinc 2-ethylcaproate, or a tetraalkylammonium compound, such as N,N,N-trimethyl-N-2-hydroxypropylammonium hydroxide or such as N,N,N-trimethyl-N-2-hydroxypropylammonium 2-ethylhexanoate.

The amounts of the starting compounds are chosen so that the isocyanate groups are in excess. The molar ratio of the polyisocyanate employed to alcohol A employed is generally from 1:1 to 30:1, preferably from 1.5:1 to 20:1.

To stabilize the free-radically polymerizable compounds (compounds I) it is preferred to add from 0.001 to 2% by weight, in particlar from 0.005 to 1.0% by weight, of polymerization inhibitors to the reaction. These compounds are the usual compounds suitable for hindering free-radical polymerization, examples being hydroquinones or hydroquinone monoalkyl ethers, 2,6-di-tert-butylphenols, such as 2,6-di-tert-butylcresol, nitrosamines, phenothiazines or phosphorous esters.

The reaction can be carried out either free from solvent or with addition of solvents. Suitable solvents are inert solvents, such as acetone, methyl ethyl ketone, tetrahydrofuran, dichloromethane, toluene, $C_1$–$C_4$-alkyl esters of acetic acid, such as ethyl acetate or butyl acetate. The reaction is preferably carried out free from solvent.

In the reaction, the corresponding isocyanates a2.5 form first of all and from these there are formed any compounds I having an allophanate group. These may react further to give compounds having more than one allophanate group, for example, the compounds of the formula I in which n is more than 1.

The progress of the reaction is judiciously monitored by means of gel permeation chromatography (GPC) or by determining the NCO content of the reaction mixture. When the reaction mixture has reached the desired composition, the reaction can be terminated by adding deactivators. Examples of suitable deactivators are organic or inorganic acids, the corresponding acid halides, and alkylating agents. By way of example, mention may be made of phosphoric acid, monochloroacetic acid, dodecylbenzenesulfonic acid, benzoyl chloride, dimethyl sulfate and, preferably, dibutyl phosphate and also di-2-ethylhexyl phosphate. The deactivators can be used in amounts of from 1 to 200 mol %, preferably from 20 to 150 mol %, based on the moles of catalyst. Usually, after the end of the reaction, remaining amounts of unreacted polyisocyanate are distilled off under reduced pressure to a level of less than 0.5%.

The reaction is customarily terminated when the reaction mixture, leaving aside any remaining amounts of the polyisocyanate employed, has the following composition:

compound I having 1 allophanate group: 1 to 100, preferably 5 to 80% by weight,
isocyanates a2.5: 0 to 50, preferably 0 to 20% by weight,
isocyanates a2.1: 0 to 90, preferably 0 to 70% by weight.

The compounds I can be isolated from the reaction mixtures with the aid of customary separation techniques; for example, with the aid of gel permeation chromatography. Usually, however, this is unnecessary, since the byproducts are likewise products of value which can customarily be present in coating systems comprising the compounds I.

The compounds I or mixtures I can on the one hand be cured by exposure to high-energy radiation in the presence or absence of other free-radically polymerizable compounds having C—C double bonds, the C—C double bonds of the compounds I and, if present, of the other free-radically polymerizable compounds being polymerized in the process.

In addition, the compounds I or mixtures I can be cured by reacting the isocyanate groups in a polyaddition reaction (referred to below as isocyanate curing); for example, by adding to the compounds I or mixtures I, before they are used, further compounds or mixtures including at least one isocyanate-reactive group which reacts with the isocyanate groups in an addition reaction, or by causing such compounds to diffuse from a gaseous medium into coatings comprising the compounds I or mixtures I.

The isocyanate curing can be accelerated by raising the temperature. In general, temperatures of up to 130° C. are suitable for such curing, since at these temperatures it is possible to bring about only the isocyanate curing without the onset of polymerization of the C—C double bond.

Where the isocyanate groups are in blocked form it is usually likewise necessary to carry out the isocyanate reaction at temperatures from 40 to 200° C. in order to eliminate the protecting groups.

Even without further additives, the compounds or mixtures I can be employed as coating compositions and, specifically, as dual-cure systems, since films of these coating compositions can be cured both with the aid of high-energy radiation, with or without the addition of photoinitiators, and by means of isocyanate curing. The isocyanate curing of the coatings can also take place, for example, in contact with a medium containing a substance (W) that is reactive toward isocyanate groups. For example, substance (W) can act on films of the coating compositions when it is in the form of a gas from the ambient atmosphere, or in the form of a liquid or a substance which is applied, for example, to a solid carrier material. Possible examples are steam, ammonia or amines, which are absorbed from the gas phase and react. Also suitable are substances (W) which act from condensed phases, such as in the case of water, alcohols, amines and their solutions. Coated substrates can also cure, for example, by being dipped in liquids or wetted with liquids which contain the substances (W), in the dipped state or, respectively, in the state wetted with liquid substance (W). In order to avoid bubbles which may be formed during the reaction, the substrates are preferably radiation-cured prior to dipping. The avoidance of formation of bubbles in the case of isocyanate reactions with water by irradiation is a further advantage of the invention.

The reactive substances (W) may likewise be present on carrier materials. Examples are moist substrates such as wood, paper, foams, mineral carriers, which can then be coated directly with the compounds or mixtures I and, for example, undergo further curing reaction after UV irradiation. As a result it is possible, for example, to coat moist substrates, especially wood or mineral substrates, e.g. molded concrete slabs or fiber cement panels, without drying the substrate beforehand. In the case of curing by water vapor, just the water fraction present in the air is sufficient.

Furthermore, full thermal curing without UV curing or post-curing after UV irradiation of the compounds of the invention is possible by heating to from 100 to 280° C., preferably from 130° C. to 200° C.

The compounds I and mixtures I are usually employed in the form of radiation-curable formulations which comprise the customary auxiliaries—that is, for example, thickeners, defoamers, leveling assistants, dyes, fillers and/or pigments and, where necessary, photoinitiators and stabilizers (referred to below for short as formulations S).

A variant of the invention is formulations S comprising
a) from 5 to 95% by weight of a compound I or of a mixture I, and
b) from 95 to 5% by weight of a compound which is different from the compounds I and has a free-radically polymerizable C—C double bond (compounds S).

The compounds S frequently comprise what are known as reactive diluents or binders, as referred to, for example, in "Chemistry & Technology of UV & EB Formulations for Coatings, Inks & Paints", Vol. 1–5, Ed. P. K. T. Oldring, London 1991.

Examples of suitable reactive diluents are monomers containing vinyl groups, especially N-vinyl compounds, such as N-vinylpyrrolidone, N-vinylcaprolactam and N-vinylformamide, and also vinyl ethers, such as ethyl, propyl, isopropyl, butyl, isobutyl, tert-butyl, amyl, 2-ethylhexyl, dodecyl, octadecyl and cyclohexyl vinyl ether, ethylene glycol monovinyl and divinyl ether, di-, tri- and tetraethylene glycol monovinyl and divinyl ether, polyethylene glycol divinyl ether, ethylene glycol butyl vinyl ether, triethylene glycol methyl vinyl ether, polyethylene glycol methyl vinyl ether, cyclohexanedimethanol monovinyl and divinyl ether, trimethylolpropane trivinyl ether, aminopropyl vinyl ether, diethylaminoethyl vinyl ether and polytetrahydrofuran divinyl ether, vinyl esters such as vinyl acetate, vinyl propionate, vinyl stearate and vinyl laurate, and vinylaromatic compounds such as vinyltoluene, styrene, 2- and 4-butylstyrene, 4-decylstyrene, and also monomers containing acrylate or methacrylate groups, examples being hydroxyethyl (meth)acrylate, tripropylene glycol methyl ether (meth)acrylate, cyclohexyl (meth)acrylate, 4-tert-butylcyclohexyl (meth)acrylate, trimethylolpropane monoformal acrylate, glycerol monoformal acrylate, 4-tetrahydropyranyl acrylate, 2-tetrahydropyranylmethyl acrylate and tetrahydrofurfuryl acrylate.

Preferred reactive diluents are monofunctional or polyfunctional esters of alpha,beta-ethylenically unsaturated carboxylic acids with aliphatic monools or polyols. Examples of suitable polyol components are the abovementioned diols or polyols mentioned in connection with the alcohols A. Examples of monools are customary alcohols and their alkoxylation products with ethylene oxide or propylene oxide, examples being methanol, ethanol, ethylhexanol, tert-butylcyclohexanol, tetrahydrofurfuryl alcohol, norbornyl alcohol, lauryl alcohol, stearyl alcohol, phenoxyethyl glycol, methoxytriethylene glycol, methoxytripropylene glycol. The polyalcohols can be completely or incompletely esterified in terms of the alcohol groups per molecule with the alpha, beta-ethylenically unsaturated carboxylic acids. Examples of reactive diluents of this kind are tert-butylcyclo-hexanol acrylate, tetrahydrofurfuryl acrylate, norbornyl acrylate, lauryl acrylate, stearyl acrylate, phenoxyethyl glycol acrylate, methoxytriethylene glycol acrylate, methoxytripropylene glycol acrylate (XXX further monoalcohols and acrylates XXX) ethylene glycol di(meth) acrylate, ethylene glycol (meth)acrylate, propylene glycol di(meth)acrylate, propylene glycol (meth)acrylate, butylene glycol di(meth)acrylate, butylene glycol (meth)acrylate, 1,6-hexanediol di(meth)acrylate, diethylene glycol di(meth) acrylate, triethylene glycol di(meth)acrylate, dipropylene glycol di(meth)acrylate, tripropylene glycol di(meth) acrylate, 1,4-cyclohexanediol di(meth)acrylate and 1,4-bis (hydroxymethyl)cyclohexane di(meth)acrylate, and also trimethylolethane tri(meth)acrylate, trimethylolethane di(meth)acrylate, trimethylolpropane tri(meth)acrylate, trimethylolpropane di(meth)acrylate, ditrimethylolpropane tetra(meth)acrylate, ditrimethylolpropane tri(meth)acrylate, pentaerythritol tetra(meth)acrylate, pentaerythritol tri(meth) acrylate, dipentaerythritol tetra(meth)acrylate and dipentaerythritol penta(meth)acrylate. Preference is also given to the esters of ethoxylated polyols, examples being the polyacrylates or polymethacrylates of alkoxylated trimethylolpropane, alkoxylated ditrimethylolpropane, glycerol, pentaerythritol or dipentaerythritol.

The binders with a free-radically polymerizable C—C double bond comprise prepolymers, polymers or oligomers whose molecular weights are preferably up to 10,000, such as (meth)acrylo-functional (meth)acrylic copolymers, epoxy (meth)acrylates, polyester (meth)acrylates, polyurethane (meth)acrylates, polyether (meth)acrylates, silicone (meth) acrylates, melamine (meth)acrylates, unsaturated polyesters having maleic acid groups, and unsaturated polyurethanes having maleic acid groups.

A large number of said binders can have isocyanate-reactive groups, especially hydroxyl groups, as a result, for example, of incomplete esterification of polyols or can be present in the form of β-hydroxy(meth)acrylate groups in epoxy acrylates or as adducts of components containing isocyanate groups with excess polyols. In this way, viscosity, pot life and dual cure properties are influenced.

All compounds S can also contain amine groups up to an amine number of 250 mg KOG/g, as a result, for example, of addition of primary or secondary amines onto double bonds. Such amines are preferably aliphatic amines such as methylamine, dimethylamine, ethylamine, diethylamine, propylamine, dipropylamine, butylamine and dibutylamine and hydroxyaliphatic amines such as ethanolamine, diethanolamine, propanolamine and dipropanolamine.

The binders and reactive diluents can be used individually or in a mixture.

Suitable fillers include silicates, examples being silicates obtainable by hydrolysis of silicon tetrachloride, such as Aerosil® from Degussa, siliceous earth, talc, aluminum silicates, magnesium silicates, calcium carbonates, etc. Suitable stabilizers include typical UV absorbers such as oxanilides, triazines and benzotriazole (the latter obtainable as Tinuvin® grades from Ciba-Spezialit&tenchemie) and benzophenones. These can be used alone or together with suitable free-radical scavengers, examples being sterically hindered amines such as 2,2,6,6-tetramethylpiperidine, 2,6-di-tert-butylpiperidine or derivatives thereof, such as bis(2, 2,6,6-tetramethyl-4-piperidyl) sebacate. Stabilizers are commonly employed in amounts of from 0.1 to 5.0% by weight based on the components present in the formulation that contain activated double bonds.

Insofar as curing takes place by means of UV radiation, the formulations of the invention include at least one photoinitiator which is able to initiate the polymerization of ethylenically unsaturated double bonds. Such photoinitiators include benzophenone and its derivatives, such as 4-phenylbenzophenone and 4-chlorobenzophenone, Michler's ketone, acetophenone derivatives, such as 1-benzoylcyclohexan-1-ol, 2-hydroxy-2,2-dimethylacetophenone and 2,2-dimethoxy-2-phenylacetophenone, benzoin and benzoin ethers, such as methyl, ethyl and butyl benzoin ether, benzil ketals, such as benzil dimethyl ketal, 2-methyl-1-[4-(methylthio)phenyl]-2-morpholinopropan-1-one, anthraquinone and its derivatives, such as methylanthraquinone and tert-butylanthraquinone, acylphosphine oxides, such as 2,4,6-trimethylbenzoyldiphenylphosphine oxide, ethyl 2,4,6-trimethylbenzoylphenylphosphinate and bisacylphosphine oxides. These photoinitiators are used, where necessary, in amounts of from 0.05 to 20% by weight, preferably from 0.1 to 10% by weight and, in particular, from 0.2 to 5% by weight, based on the compounds I and S of the formulations of the invention.

In order to improve the curing rate it is possible to add amines as coinitiators. Such amines are commonly compounds such as tributylamine, triethanolamine, dimethylethanolamine and methyldiethanolamine. They are used in amounts of from 1 to 10% by weight, based on the solids content of the coating material. Likewise suitable are binders containing amino groups, as can be prepared, for example, by addition of aliphatic or hydroxyaliphatic primary or secondary amines, such as methylamine, dimethylamine, ethylamine, diethylamine, propylamine, dipropylamine, butylamine, dibutylamine, ethanolamine, diethanolamine, propanolamine and dipropanolamine, onto acrylic ester monomers and acrylic ester binders of the compound S type.

Amine-modified products of this kind may also serve as principal binder and can be used in a formulating proportion of up to 98% by weight.

Where the formulation of the invention is cured by means of electron beams, photoinitiators can be dispensed with.

When employing electron beam curing, UV curing in combination with suitable photoiniators, or thermal curing, the formulations of the invention may also comprise pigments.

It is possible to employ the formulations S directly as coating compositions. In a further embodiment of the invention, the formulations S are used to prepare 2-component coating compositions by adding to said formulations S, before processing, a compound having isocyanate-reactive groups (such compounds being referred to below for short as compounds R).

Where the isocyanate groups which carry the components of the formulation S are not blocked, the two components are judiciously mixed at the latest 24 h before the coating composition is applied to the article that is to be coated.

Customarily, the ratio of the isocyanate groups to the isocyanate-reactive groups is from 2:1 to 0.5:1, preferably from 10:1 to 0.7:1 and, with particular preference, from 0.9:1 to 1.1:1.

The compounds R are generally those which are present as the A component in conventional 2-component polyurethane coating compositions; in other words, for example, they are low molecular mass alcohols having 2 to 20 carbon atoms and 2 to 6 OH groups, or hydroxy-functional polymers (referred to below for short as "polymers (A)").

Examples of the polymers (A) are polymers having a hydroxyl content of from 0.1 to 20% by weight, preferably from 0.5 to 10% by weight. The number-average molecular weight Mn of the polymers is preferably from 1000 to 100,000, with particular preference from 2000 to 10,000. The polymers are preferably those which consist to the extent of more than 50% of $C_1$–$C_{20}$-alkyl (meth)acrylate, vinylaromatic compounds having up to 20 carbon atoms, vinyl esters of carboxylic acids having up to 20 carbon atoms, vinyl halides, nonaromatic hydrocarbons having 4 to 8 carbon atoms and 1 or 2 double bonds, unsaturated nitrites, and mixtures thereof. Particular preference is given to polymers which consist to the extent of more than 60% by weight of $C_1$–$C_{10}$-alkyl (meth)acrylates, styrene or mixtures thereof.

Furthermore, the polymers (A) include hydroxy-functional monomers in accordance with the above hydroxyl content and, if desired, include further monomers, examples being ethylenically unsaturated acids, especially carboxylic acids, acid anhydrides or acid amides.

Examples of further polymers (A) are polyesterols as obtainable by condensing polycarboxylic acids, especially dicarboxylic acids, with polyols, especially diols.

Further suitable polymers (A) are polyetherols, which are prepared by subjecting ethylene oxide, propylene oxide or butylene oxide to addition reaction with H-active components. Polycondensates prepared from butanediol are also suitable.

The polymers (A) can of course also be compounds having primary or secondary amino groups.

By way of example, mention may be made of Jeffamines, i.e., amino-terminated polyetherols or oxazolidines.

Further suitable compounds R are hydroxy-functional acrylic ester compounds as formed, for example, by incomplete esterification of polyols, polyetherols or polyesterols or as present in the form of β-hydroxy (meth)acrylate groups in epoxy acrylates or as prepared as adducts of components containing isocyanate groups with excess polyols.

The compounds I, mixtures I, formulations S and 2-component coating systems of the invention (referred to below for short as coating compositions) are suitable as coating compositions for a variety of substrates.

The formulations of the invention are found to be particularly suitable for coating substrates such as wood, wood-base materials, paper, textile, leather, nonwoven, plastics surfaces, glass, ceramic, mineral building materials, such as molded cement slabs and fiber cement slabs, and especially metals or corresponding precoated substrates.

Accordingly, the present invention also provides a method of coating substrates, especially metals or coated metals, as they are employed, for example in the car bodywork or coil coating area, and the coated substrates obtainable by this method. The substrates are generally coated by applying at least one radiation-curable formulation of the invention to the target substrate in the desired thickness and removing any solvent present. If desired, this procedure can be repeated one or more times. The radiation-curable formulations are applied to the substrate in a conventional manner, for example, by immersing, spraying, troweling, knifecoating, brushing, rolling, rollercoating or flowcoating.

Sheets made of paper or plastic, for example, coated in accordance with the invention can likewise be applied to substrates by lamination, with or without the aid of an adhesive, both on the part of the backing material and on the part of the coating, or by backspraying. The films partially cured either photochemically or thermally can be shaped before, during or after the application. Consequently, sheet coatings on nonplanar substrates, or the shaping of the coated substrates, are possible.

The coating thickness is generally within a range from 3 to 3000 g/m² and, preferably, from 10 to 2900 g/m². An advantage of the coatings of the invention, especially on the basis of the liquids which can be processed at low viscosity and without solvent, is the simple preparation of thick layers, free from air bubbles, in one operation. Application can be made either at room temperature or at elevated temperature, preferably not above 200° C. In the case of thick layers of more than 100 μm, which are precured thermally, curing temperatures below 100° C., especially below 60°C., are preferred in order to avoid air bubbles.

In general, the coatings are subsequently cured, both by exposure to high-energy radiation and by reacting the isocyanate groups with atmospheric moisture or compounds R. This procedure is termed the dual-cure process.

Unlike radiation curing, which takes place within a few seconds or fractions of seconds, isocyanate curing is generally slow, i.e., at room temperature it is often not over until days have passed. However, it can also be accelerated by selecting suitable catalysts, at elevated temperature, preferably up to 200° C., or by adding suitable reactive co-reactants. At curing temperatures above 120° C. it is possible for the reactive double bonds to react likewise without the addition of thermal initiators and to contribute to curing, so that an additional irradiation can be dispensed with. Curing temperatures for the polymerization of the double bonds without irradiation can be lowered by adding polymerization initiators which form free radicals as a result of heat, such as, for example, organic peroxide or azo compounds, alone or in combination with accelerators based on cobalt compounds and/or amines, to below room temperature.

If two or more coats of the coating material are applied atop one another, it is possible if desired to carry out radiation curing after each coating operation.

Radiation curing takes place by exposure to high-energy radiation, i.e. UV radiation or daylight, preferably light with a wavelength from 250 to 600 nm, or by irradiation with high-energy electrons (electron beams; 150 to 300 keV). Examples of the radiation sources used are high-pressure mercury vapor lamps, lasers, pulsed lamps (flashlights), halogen lamps or excimer sources. In the case of UV curing, the radiation dose which is usually sufficient for crosslinking lies within the range from 80 to 3000 mJ/cm². Using suitable photoinitiators which absorb in the longwave region, especially with acylphosphine oxides, 2,4,6-trimethylbenzoyldiphenylphosphine oxide, ethyl 2,4,6-benzoylphenylphosphinate and bisacylphosphine oxides, it is possible for coatings to cure even under daylightlike light sources or in sunlight.

In a particularly efficient manner in terms of energy consumption, photoinitiator requirement and surface quality, especially scratch resistance and chemical resistance, if desired, the irradiation can also be conducted in the absence of oxygen: for example, under an inert gas atmosphere, or under atmospheres with reduced oxygen contents of below 17% by weight. Suitable inert gases are preferably nitrogen, noble gases, carbon dioxide, or combustion gases. The irradiation can also be carried out with the coating composition covered with transparent media. Examples of transparent media are polymer films, glass or liquids, e.g., water.

In one preferred method curing is carried out continuously by passing the substrate, treated with the formulation of the invention, at constant speed past a radiation source. This requires the curing rate of the formulation of the invention to be sufficiently high.

This difference in the progress of curing over time can be exploited in particular when the coating of the article is followed by another processing step in which the film surface enters into direct contact with another article or is worked mechanically.

In this case, the procedure comprises

Ia. in step Ia, coating an article with a film of the coating composition,

IIa. in step IIa, exposing the film of the coating composition is to high-energy radiation, the film being precured, IIIa. in step IIIa, working, especially deforming, overcoating with a further or several coatings, the article coated with the precured film of the coating composition, or bringing the surface of the precured film into contact with another article, and IVa. in step IVa, fully curing the precured film of the coating composition with which the worked article is coated, by means of isocyanate curing;

or, in accordance with a second method, it comprises

Ib. in step Ib, coating an article with a film of the coating composition,

IIb. in step IIb, precuring the film of the coating composition with which the article is coated by reacting the isocyanate groups in a polyaddition reaction, IIIb. in step IIIb, working, especially deforming, overcoating with a further or several coatings, the article coated with the precured film of the coating composition, or bringing the surface of the precured film into contact with another article, and IVb. in step IVb, exposing the precured film of the coating composition to high-energy radiation, in the course of which the film is fully cured.

The advantage of these methods is that the coated articles can be processed further directly following step IIa or IIb, respectively, since the surface can be formulated to be tack-free or else tacky. The precured film is still sufficiently flexible and extensible that the article can be shaped without the film flaking off or tearing in the process. In the case of freedom from tack, in particular, direct mechanical operations such as forming or grinding are possible without the sandpaper sticking.

The dual-cure process may prove advantageous even if it is not intended to deform the article, since the articles provided with the precured film are particularly easy to transport and store, in the form of stacks, for example. Furthermore, the dual-cure process offers the advantage that the coating compositions are able to undergo chemical aftercuring in dark regions (regions inaccessible to the radiation) and so still attain sufficient material properties independently of the irradiation. Furthermore, spray mist deposits cure without tack or emissions. These coating compositions are therefore particularly suitable for use as sealing compounds with rapid curing at areas accessible to illumination and post-curing in dark regions.

Material absorbed into substrates, or, generally, when using absorbent, porous substrates such as wood, paper, mineral substrates, textiles, leather, foams, material which has penetrated, is cured, so preventing emittable, migratable or extractable fractions.

Subsequent to step III, step IVa is frequently realized by storing the coated articles in air for a further few days at room temperature or elevated temperature in order to accelerate the curing process. During this time, as described above, the isocyanate groups react with atmospheric humidity or, if present, with the A component, and the network density increases and the film acquires its ultimate service properties.

The compounds I, mixtures I or a formulation S can be employed in particular as casting resin, troweling compound, sealing compound, solder resist, photoresist resin, stereolithography resin, printing ink, adhesive, dental compound, for producing photopolymeric printing plates, as a resin for composite materials or as a coating for vehicle coating, in particular for coating bodywork parts.

For the applications as a photoresist resin, solder resist, stereolithography resin and photopolymeric printing plate, the property of the locally defined curability by means of irradiation through masks or by means of punctiform beam bundles, e.g., laser radiation, is critical. By this means it is possible to produce a relief in a washing process which uses solvents or aqueous washing liquids and is conducted after the imaging radiation curing. By means of thermal postcuring of the photopolymerized compositions, higher mechanical and chemical resistances are obtained, which are required for use, for example, as a printing plate, circuitboard or other molding.

EXPERIMENTAL SECTION

1. Preparation of the Compounds I 1.1. Preparation of Polyisocyanato Acrylates 1–9 containing urethane and allophanate groups, and of Comparative Example 1 (C1), from HDI and unsaturated monoalcohols Hexamethylene diisocyanate (HDI) was introduced under nitrogen blanketing into the reaction vessel and the amount of stabilized OH component specified in Table 1 was added. The mixture was heated to 80° C. and 200 ppm by weight (based on diisocyanate) of the catalyst N,N,N-trimethyl-N-(2-hydroxypropyl)ammonium 2-ethylhexanoate were added. The temperature slowly rose to 120° C. The reaction was conducted at this temperature and stopped, when the NCO content reached the level specified in Table 1, by adding 250 ppm by weight (based on diisocyanate) of di-2-ethylhexyl phosphate. The reaction mixture was subsequently freed from unreacted HDI in a thin-film evaporator at 135° C. and 2.5 mbar.

Data relating to the end products are given in Table 1.

1.2. Preparation of the Polyisocyanato Acrylate 10 Containing Urethane and Allophanate Groups Hexamethylene diisocyanate (HDI) was introduced under nitrogen blanketing into the reaction vessel and the amount of stabilized 3-(acryloyloxy)-2-hydroxypropyl methacrylate specified in Table 1 was added. The mixture was heated to 80° C. and 500 ppm by weight (based on diisocyanate) of the catalyst zinc acetylacetonate were added. The temperature was subsequently raised slowly to 120° C. The reaction was conducted at this temperature and stopped, when the NCO content reached the level specified in Table 1, by adding 550 ppm by weight (based on diisocyanate) of di-2-ethylhexyl phosphate. The reaction mixture was subsequently freed from unreacted HDI in a thin-film evaporator at 135° C. and 2.5 mbar.

Data relating to the end product are given in Table 1.

1.3. Preparation of Polyisocyanato Acrylates 11 and 12 Containing Urethane and Allophanate Groups, From IPDI or 1,3-BIC and Unsaturated Monoalcohols The diisocyanates were introduced under nitrogen blanketing into the reaction vessel and the amount of stabilized OH component specified in Table 1 was added. The mixture was heated to 100° C. and 200 ppm by weight (based on diisocyanate) of the catalyst N,N,N-trimethyl-N-(2-hydroxypropyl)ammonium 2-ethylhexanoate were added. The temperature slowly rose to 120° C. The reaction was conducted at this temperature and stopped, when the NCO content reached the level specified in Table 1, by adding 250 ppm by weight (based on diisocyanate) of di-2-ethylhexyl phosphate. The reaction mixture was subsequently freed from unreacted isocyanate in a thin-film evaporator at 135° C. and 2.5 mbar.

Data relating to the end products are given in Table 1.

1.4. Comparative Experiments, Preparation of Urethane Acrylates in Analogy to EP 549 116 from HDI Polyisocyanate and HEA (Hydroxyethyl Acrylate)

625 g (1 mol) of HDI polyisocyanate having an average functionality of about 3.5 and an NCO content of 22.0% by weight (BASONAT®HI 100, BASF AG) were introduced under nitrogen blanketing into a reaction vessel, 200 ppm of dibutyltin dilaurate were added, and the mixture was heated to 55° C. Over the course of 15 minutes the amounts of hydroxyethyl acrylate (stabilized) specified in Table 2 were added and the batch was heated slowly to 80° C. Thereafter it was stirred at 80° C. for one hour more.

Data relating to the coating compositions of the prior art are given in Table 2

| Abbreviations: | |
|---|---|
| HDI | Hexamethylene diisocyanate |
| IPDI | Isophorone diisocyanate |
| 1,3-BIC | 1,3-bis (isocyanatomethyl) cyclohexane |
| HEA | Hydroxyethyl acrylate |
| HPA | Hydroxypropyl acrylate |
| HEMA | Hydroxyethyl methacrylate |
| GAMA | 3-(acryloyloxy)-2-hydroxypropyl methacrylate |
| DBTL | Dibutyltin dilaurate |

2. Production and Testing of Coating Formulations From the Polyisocyanates of the Invention, as 1-Component Coating Systems Where they had a viscosity of more than 500 mpas, the products of the invention and comparative products were diluted with butyl acetate (BuAc) to 500 mpas. The samples were applied to glass or sheet metal using film-drawing frames.

The products of the invention and comparative products were cured and tested in different ways:

UV Radiation:

The films, flashed off at room temperature if desired to remove the solvent, are irradiated under an IST high-pressure mercury lamp (120 W/cm) five times at a belt speed of 10 m/min.

Moisture Curing:

The films are stored for several days at room temperature and 50% atmospheric humidity.

Table 3 describes the result after curing with atmospheric humidity only

Table 4 describes the result after curing with atmospheric humidity and UV curing Test Methods:

Pendulum attenuation (PA, in number of swings): coating material on glass as substrate (DIN 53157) with a dry film thickness of about 30 µm in the case of air curing and about 50 µm in the case of UV curing.

Erichsen indentation (EI; DIN 53156, in mm indentation): coating material on Bonder metal panel 132 (dimensions 190×105×1 mm from Chemetall). Film thickness 25 to 30 µm.

Adhesion with crosshatching (AwC; DIN 53151, in points): Coating material on Bonder metal panel 132 (dimensions 190×105×1 mm from Chemetall). Dry film thickness 25 to 30 µm. The assessment is made with the aid of a scale of points from 0 to 5 (0=best rating)

3. Two-component Coating Systems With the Addition of NCO-reactive Compounds

Product No. 6 of the invention (see Tables 1 and 5) was mixed with the hydroxy-functional vinyl polymer (Lumitol® H 136, BASF), firstly in accordance with the stoichiometric OH/NCO ratio, then in equal proportions for the comparative experiment. As a comparison, a clearcoat based on the same acrylate resin in combination with the polyisocyanate hardener (Basonat® P LR 8901, BASF) was tested. Adjustment to the application viscosity of 20 s (DIN 53 211 cup 4 mm efflux nozzle) was carried out using butyl acetate.

Coatings with a wet film thickness of 200 mm were applied to glass plates using a film-drawing frame. The clearcoats obtained in this way were cured under standard climatic conditions.

The films, with the solvent removed by flashing off at room temperature, are irradiated under an IST high-pressure mercury lamp (120 W/cm) nine times at a belt speed of 15 m/min.

The properties of the resulting coatings are summarized in Tables 6 and 7.

TABLE 1

Reaction products of isocyanates and unsaturated monoalcohols

| Product No. | Isocyanate | Monoalcohol | Amount based on isocyanate (mol %) | NCO content of the mixture (% by weight) | NCO content after distillation (% by weight) | Viscosity at 23° C. (mPas) |
|---|---|---|---|---|---|---|
| 1 | HDI | HEA | 5 | 40.8 | 20.1 | 520 |
| 2 | HDI | HEA | 10 | 39.0 | 18.5 | 310 |
| 3 | HDI | HEA | 15 | 35.6 | 17.4 | 290 |
| 4 | HDI | HEA | 20 | 33.3 | 16.7 | 260 |
| 5 | HDI | HEA | 20 | 26.7 | 15.8 | 1790 |
| 6 | HDI | HEA | 40 | 21.6 | 13.5 | 810 |
| 7 | HDI | HEA | 50 | 16.8 | 11.8 | 1640 |
| 8 | HDI | HPA | 20 | 32.8 | 16.0 | 345 |
| 9 | HDI | HEMA | 30 | 23.2 | 14.2 | 1290 |
| 10 | HDI | GAMA | 20 | 36.8 | 12.8 | 890 |
| 11*) | IPDI | HEA | 20 | 30.1 | — | 5680 |

TABLE 1-continued

Reaction products of isocyanates and unsaturated monoalcohols

| Product No. | Isocyanate | Monoalcohol | Amount based on isocyanate (mol %) | NCO content of the mixture (% by weight) | NCO content after distillation (% by weight) | Viscosity at 23° C. (mPas) |
|---|---|---|---|---|---|---|
| 12 | 1,3-BIC | HEA | 20 | 30.4 | 15.0 | 27,500 |
| C1 (Comparative) | HDI | Allyl alcohol | 20 | 34.0 | 17.8 | 240 |

*): The reaction mixture was not distilled

TABLE 2

Urethane acrylates as comparative products

| Comparison No. | Amount of HEA (g) | Mol of HEA | HEA proportion (% by weight) | NCO content (% by weight) | Viscosity 23° C. (mPas) |
|---|---|---|---|---|---|
| C2 | 75.6 | 0.65 | 10.8 | 15.3 | 12,220 |
| C3 | 116.0 | 1.0 | 15.7 | 13.2 | 24,200 |
| C4 | 232.0 | 2.0 | 27.1 | 6.2 | 220,000 |

C2 was prepared as specified in EP 549 116; the products C3 and

C4 were prepared to a higher double bond content.

The proportion of acrylate in these products is lower than in the compounds I of the invention (proportion in the simplest allophanate=25.7% by weight), and yet the viscosities are already very high.

Increasing the scratch resistance in comparison to an automotive clearcoat

K1) 50 parts of an allophanate adduct of HEA and HDI with 12.1% NCO and a viscosity of 1 Pas with the auxiliaries system comprising 1 part of a 1% strength dibutyltin dilaurate solution in butyl acetate, 2 parts of a mixture of Irgacure 184 (Ciba Spezialitätenchemie) and 0.5 parts of Lucirin TPO (BASF AG) (ratio 8.75:1.25), 0.5 part of Tinuvin 292 (Ciba S.) and 0.75 part of Tinuvin 400 (Ciba S.) are applied with a film thickness of 50 μm to a glass plate. The film is irradiated twice under a UV high-pressure mercury lamp (120 W/cm) with a belt speed of 5 m/min. It is then heated at 130° C. for 30 minutes.

A sponge laden with silicon carbide is moved over the cooled coating film under the load of a hammer weighing 500 g. The loss in gloss measured at 60° after different numbers of strokes was determined as a measure of the sensitivity to scratching.

K2) In a procedure similar to that of K1), a film was prepared from 44.7 parts of the allophanate acrylate with 6.54 parts of 1,2-propanediol and with the auxiliaries system of 1) and was tested.

K3) In a procedure similar to that of K1), a film was prepared from 39.4 parts of the allophanate acrylate with 10.6 parts of a polyetherol comprising the adduct of 1 mol of trimethylolpropane with 3 mol of ethylene oxide (Lupranol VP 9236) and with the auxiliaries system of 1) and was tested.

| Composition Example | K1 | K2 | K3 |
|---|---|---|---|
| Allophanate acrylate (12.1% NCO, visc. 1 Pas) | 50 | 44.7 | 39.4 |
| 1,2-Propanediol | | 6.54 | |
| Lupranol VP 9236 | | | 10.6 |

The system used for comparison was a solventborne two-component polyurethane coating material (2K PU) from Automotive OEM Finishing (BASF Coatings AG) which was baked analogously at 130°/30 minutes.

| | Number of double strokes | | |
|---|---|---|---|
| 60° gloss | 0 | 10 | 50 |
| Example K1 | 90 | 70 | 63 |
| Example K2 | 96 | 59 | 44 |
| Example K3 | 95 | 84 | 73 |
| 2K PU | 89 | 36 | 14 |

The isocyanatoacrylate coating materials exhibit a significantly lower loss of gloss and thus greater scratch resistance. They are suitable for automotive finishing. Example K1 has the additional advantage that it can be processed as a one-component coating material.

Priming of Wood to Reduce Extractable Constituents

G1) UV roller varnishing of beech veneer with conventional UV varnish

| Varnish 1 (comparative): | 60 parts of | polyester acrylate (Laromer PE 56F) |
|---|---|---|
| | 40 parts of | tripropylene glycol diacrylate (TPGDA) |
| | 4 parts of | Irgacure 184 (photoinitiator from Ciba Spezialitätenchemie) |
| | 1 part of | benzophenone |
| | 1 part of | CAB 551-001 (cellulose acetobutyrate from Kodak) |
| | Viscosity: | 1.2 Pas |

Varnish 1 is applied to beech veneer at 26 g/m² as a primer and is UV-cured at 10 m/min, followed by the application of a further 24 g/m² and final UV curing at 5 m/min.

In order to determine the extractable fractions (3 days after application), 15 cm² of the coated veneer are comminuted and extracted with 10 ml of methylene chloride (covering) in a Duran flask at 40° C. for 1 h.

In terms of extractable acrylate constituents, TPGDA was determined by means of GC/MS at 1330 mg/m² of veneer.

G2) UV roller varnishing of beech veneer with varnish of the invention

| Varnish 2: | 100 parts of | allophanate adduct of HDI and HEA NCO value 12.8%, viscosity 1 Pas |
| --- | --- | --- |
| | 4 parts of | Irgacure 184 |
| | Viscosity: | 1.6 Pas |

Varnish 2 is applied to beech veneer at 25 g/m² as a primer and is UV-cured at 2 m/min to give a tack-free layer, after which 23 g/m² of varnish 1 are applied and UV curing is carried out twice at 2 m/min.

Extractable fractions of acrylates are below the detection limit (<10 mg/m²).

Example Relating to UV Roller Varnishing and Forming

Varnish 2) (see K2) is applied at 80g/m² to cherry veneer and UV-cured twice at 2 m/min.

Using a sizing resin sheet, the veneer is pressed onto a profiled substrate with a profiled counterformer at 100 kp/cm2 and at 120° C. The deformability of the varnish layer is sufficient for the shaping of the veneer, and the layer only tears when the varnish is damaged.

Example Relating to the Preparation of Thick, Deformable and Post-curable Films 20.76 parts of an allophanate adduct of HEA and HDI with 12.1% NCO and a viscosity of 1 Pas are blended with 33.33 parts of Luprenal VP 9236 (BASF, ethoxylated trimethylolpropane, OH number 605 mg KOH/g), 0.91 part of propylene glycol and 0.5 part of a 1% strength solution of dibutyltin dilaurate in butyl acetate and with 1 part of a mixture of Irgacure 184 (Ciba Spezialitätenchemie) and Lucirin TPO (BASF) (weight ratio 3.5:0.5) in such a way as to ensure absence of air bubbles. The varnish is poured into a polyethylene dish to give a film 3 mm high. For curing, the varnish is stored in the absence of light at room temperature for 1 hour and at 60° C. for 30 minutes and also at room temperature for 24 hours. The result is an elastomeric, transparent and bubble-free thick film which does not produce any bubbles, and does not flow, even when heated to 130° C. Following UV irradiation at 2*5 m/min belt speed under a 120 W/cm high-pressure mercury lamp, the elastomer film hardens to a highly resistant, transparent thermoset body.

Preparing a High-hiding Red-pigmented Paint Film 62.4 parts of an allophanate adduct of HEA and HDI with 12.1% NCO and a viscosity of 1 Pas are dispersed with 3 parts of butyl acetate, 9 parts of Disperbyk 163 (from Byk) and 30 parts of Irgazin DPP Red BO in a Skandex disperser mixing apparatus by means of 150 parts of zirconium beads for 1 hour to give a pigment paste, which is then sieved. 50 parts of this paste are blended with 3.6 parts of a mixture of trimethylolpropane and propylene glycol (weight ratio 2:1), 0.13 part of Byk 307 (from Byk) and 1.07 part of a 1% strength solution of dibutyltin dilaurate in butyl acetate and with 2 parts of a mixture of Irgacure 184 (Ciba Spezialit ätenchemie) and Lucirin TPO (BASF) (weight ratio 3.5:0.5). 50 μm of film are drawn down onto a glass plate using a coating bar and the film is heated at 80° C. for 15 minutes.

Following UV irradiation at 2*5 m/min belt speed under a 120 W/cm high-pressure mercury lamp, the film surface hardens without developing surface defects, although these are developed when the film is irradiated, without heating, directly following its application.

Preparing a High-hiding, Red-pigmented Thermoformable and Inertly Exposable Paint Film The red-pigmented paint of the last example, albeit with a greatly reduced proportion (0.25 part) of the photoinitiator from the above example, is applied in a thickness of 50 μm to a thermoformable polypropylene sheet and heated at 80° C. for 15 minutes.

This film assembly can be pulled without folds over a nonplanar surface, e.g. a tabletop corner, and pressed on. The thermoformability is retained if the sheet is stored protected from light. In order to increase the bond strength, it is possible to use an additional adhesive layer either on the substrate or on the painted sheet or on both. Following UV irradiation at 10 m/min belt speed under a 120 W/cm high-pressure mercury lamp, the film surface hardens to a highly resistant, weather-resistant and scratch-resistant coating.

A further improvement, in particular in respect of the optical appearance and resistance properties, is obtained if, as a deformable topcoat layer, a clearcoat corresponding to the example relating to the preparation of thick-layer deformable and post-curable films is additionally applied between polypropylene sheet and paint film.

Example Relating to the Preparation of a Photostructured Relief 50 parts of an allophanate adduct of HEA and HDI with 12.1% NCO, viscosity 1 Pas, are blended with 0.5 part of a 1% strength solution of dibutyltin dilaurate in butyl acetate and with 1 part of a mixture of Irgacure 184 (Ciba Spezialit ätenchemie) and Lucirin TPO (BASF) (weight ratio 3.5:0.5). The mixture is applied in a layer thickness of 40 μm to a polyester sheet, covered with an image mask and subjected to UV exposure at a belt speed of 5 m/min. Subsequently, uncured material is washed out with acetone. Exposed areas remain as a relief. When stored in air, the relief post-cures by means of atmospheric humidity and becomes harder and more resistant to swelling.

We claim:

1. A compound having isocyanate groups with or without blocking, allophanate groups and free-radically polymerizable C—C double bonds, the C—C double bonds being in activated form by virtue of a carbonyl group attached directly to them or by virtue of an oxygen atom in an ether function (activated double bonds), derived from polyisocyanates and alcohols A which in addition to the alcohol group also have an activated double bond.

2. A compound as claimed in claim 1 of the formula I

OCN—R¹—(—R²—C(O)—R²—R¹—)ₙ—NCO        I in which n is an integer from 1 to 10,

R¹ is a divalent aliphatic or alicyclic $C_2$–$C_{20}$ hydrocarbon unit or an aromatic $C_5$–$C_{20}$ hydrocarbon unit R² in each repeating unit is —NH— once and N—C(O)— R³ once, R³ being a radical derived from an alcohol A having at least one hydroxyl group by abstracting a hydrogen atom of an alcoholic hydroxyl group and the alcohol A having at least one functional group including, in addition to the alcohol groups, an activated double bond.

3. A compound as claimed in claim 1, wherein the alcohol A is an ester of an aliphatic or aromatic polyol and an acrylic or methacrylic acid, an amide of an amino alcohol and an acrylic or methacrylic acid, or a vinyl ether prepared from an aliphatic or aromatic polyol.

4. A compound as claimed in claim 3, wherein the aliphatic or aromatic polyol is a diol, triol or tetrol of 2 to 20 carbon atoms or a polyether polyol or polyester polyol or a polyacrylate polyol having an average OH functionality of from 2 to 10.

5. A compound as claimed in claim 2, wherein the radical $R^3$ is derived from hydroxyethyl acrylate, hydroxypropyl acrylate, hydroxybutyl acrylate, hydroxyethyl methacrylate or 3-(acryloyloxy)-2-hydroxypropyl methacrylate.

6. A compound as claimed in claim 1, wherein the polyisocyanates are selected from the group consisting of hexamethylene diisocyanate, isophorone diisocyanate, tetramethylxylylene diisocyanate, di(isocyanatocyclohexyl) methane and 1,3-bis(isocyanatomethyl)cyclohexane.

7. A mixture I comprising
   a1) from 1 to 100% by weight of compound I of claim 2
   a2) from 0 to 99% by weight of another compound having one or more isocyanate groups and a functional group selected from the group consisting of urethane, urea, biuret, allophanate, carbodiimide, uretonimine, uretdione and isocyanurate groups.

8. A mixture as claimed in claim 7, wherein the activated double bond content, based on the overall amount of the co-components a1 and a2, is from 0.02 to 20% by weight.

9. A mixture as claimed in claim 7, wherein the isocyanate group content of components a1 and a2, based on the overall amount of co-components a1 and a2, is from 0.1 to 40% by weight.

10. A mixture as claimed in claim 7, wherein the ratio of the activated double bonds to the isocyanate groups of the coomponents a1 and a2 is from 50:1 to 0.02:1.

11. A formulation comprising
   a) from 1 to 99% by weight of a compound I of claim 2, and
   b) from 99 to 1% by weight of a compound which is different from the compound I and has a free-radically polymerizable C—C double bond.

12. A 2-component coating composition comprising the compound of claim 1 and at least one compound having at least one isocyanate-reactive group , with the proviso that the ratio of the isocyanate groups to the isocyanate-reactive groups is from 200:1 to 0.5:1.

13. A process for preparing a compound as claimed in claim 1, which comprises reacting a diisocyanate with an alcohol having, in addition to the alcohol group, an activated double bond at a temperature from 80 to 280° C.

14. A coating method which comprises coating an article with a coating comprising compound I as claimed in claim 2, curing the coating in a polyaddition reaction of the isocyanate groups at room temperature or at increased temperature, and, optionally exposing the coating composition to high-energy radiation at the beginning of, during or after the polyaddition reaction.

15. A coating method which comprises coating an article with a coating comprising compound I as claimed in claim 2, and heating the coating composition to a temperature of up to 200° C.

16. A coating method which comprises coating an article with a coating comprising compound I as claimed in claim 2 exposing the coating to high-energy radiation, and optionally curing the coating in an atmosphere which comprises water vapor, ammonia or amines.

17. A coated article prepared by the coating method as claimed in claim 14.

18. A casting resin, troweling compound, sealing compound, stereolithography resin, solder resist, radiation-curable photopolymeric printing plate composition, photoresist, printing ink, adhesive, dental compound or resin for composite materials comprising the compound I of claim 2.

19. A formulation S comprising
   a) from 1 to 99% by weight of a mixture I of claim 7, and
   b) from 99 to 1% by weight of a compound which is different from the compound I and has a free-radically polymerizable C—C double bond (compound S).

20. A coating method which comprises coating an article with a coating comprising a mixture I as claimed in claim 7, curing the coating in a polyaddition reaction of the isocyanate groups at room temperature or at increased temperature, and, optionally exposing the coating composition to high-energy radiation at the beginning of, during or after the polyaddition reaction.

21. A coating method which comprises coating an article with a coating comprising a formulation as claimed in claim 11, curing the coating in a polyaddition reaction of the isocyanate groups at room temperature or at increased temperature, and, optionally exposing the coating composition to high-energy radiation at the beginning of, during or after the polyaddition reaction.

22. A coating method which comprises coating an article with a coating comprising a 2-component coating composition as claimed in claim 12, curing the coating in a polyaddition reaction of the isocyanate groups at room temperature or at increased temperature, and, optionally exposing the coating composition to high-energy radiation at the beginning of, during or after the polyaddition reaction.

23. A coating method which comprises coating an article with a coating comprising a mixture I as claimed in claim 7, and heating the coating to a temperature of up to 200° C.

24. A coating method which comprises coating an article with a coating comprising a formulations as claimed in claim 11, and heating the coating to a temperature of up to 200° C.

25. A coating method which comprises coating an article with a coating comprising a coating composition as claimed in claim 12, and heating the coating to a temperature of up to 200° C.

26. A coating method which comprises coating an article with a coating comprising a mixture I as claimed in claim 7, exposing the coating to high-energy radiation, and optionally curing the coating in an atmosphere which comprises water vapor, ammonia or amines.

27. A coating method which comprises coating an article with a coating comprising a formulation as claimed in claim 11, exposing the coating to high-energy radiation, and optionally curing the coating in an atmosphere which comprises water vapor, ammonia or amines.

28. A coating method which comprises coating an article with a coating comprising a coating composition as claimed in claim 12, exposing the coating to high-energy radiation, and optionally curing the coating in an atmosphere which comprises water vapor, ammonia or amines.

29. A coated article prepared by the coating method as claimed in claim 20.

30. A coated article prepared by the coating method as claimed in claim 21.

31. A coated article prepared by the coating method as claimed in claim 22.

32. A casting resin, troweling compound, sealing compound, stereolithography resin, solder resist, radiation-curable photopolymeric printing plate composition, photoresist, printing ink, adhesive, dental compound or resin for composite materials comprising the mixture I of claim 7.

33. A casting resin, troweling compound, sealing compound, stereolithography resin, solder resist, radiation-curable photopolymeric printing plate composition, photoresist, printing ink, adhesive, dental compound or resin for composite materials comprising the formulation of claim 11.

34. A casting resin, troweling compound, sealing compound, stereolithography resin, solder resist, radiation-curable photopolymeric printing plate composition, photoresist, printing ink, adhesive, dental compound or resin for composite materials comprising the 2-component coating composition of claim 12.

* * * * *